United States Patent [19]

Costa et al.

[11] Patent Number: 5,248,678
[45] Date of Patent: Sep. 28, 1993

[54] METHODS FOR INCREASING AROUSAL AND ALERTNESS AND FOR THE AMELIORATION OF COMATOSE STATES

[75] Inventors: Jonathan L. Costa, Wheaton, Ill.; Hernan V. Salazar; Jesus A. Diazgranados, both of Cali, Colombia

[73] Assignee: Fractal Laboratories, Inc., Newton, N.J.

[21] Appl. No.: 906,585

[22] Filed: Jun. 30, 1992

[51] Int. Cl.$^5$ .................. A61K 31/52; A61K 31/55
[52] U.S. Cl. ............................. 514/220; 514/221; 514/250; 514/263; 514/264; 514/293; 514/450
[58] Field of Search ............... 514/250, 220, 221, 263, 514/264, 293, 450

[56] References Cited

U.S. PATENT DOCUMENTS

| | | | |
|---|---|---|---|
| 4,171,314 | 10/1979 | Chabala et al. | 260/343.41 |
| 4,173,571 | 11/1979 | Chabala et al. | 260/343.41 |
| 4,199,569 | 4/1980 | Chabala et al. | 424/180 |
| 4,201,861 | 5/1980 | Mrozik et al. | 536/17 A |
| 4,206,205 | 6/1980 | Mrozik et al. | 424/180 |
| 4,310,519 | 1/1982 | Albers-Schonberg et al. | 424/181 |
| 4,333,925 | 6/1982 | Buhs et al. | 424/181 |
| 4,495,187 | 1/1985 | Sarges | 514/250 |
| 4,547,501 | 10/1985 | Sarges | 514/250 |
| 4,963,667 | 10/1990 | Chiu et al. | 536/7.1 |
| 5,189,026 | 2/1993 | Costa | 514/30 |

OTHER PUBLICATIONS

Caronna, Rehabilitation of the Head Injured Adult, Rosenthal et al, eds., F. A. Davis Co., Philadelphia, Pa. Chapter 5, 59-73 (1983).
Adams, et al., Principles of Neurology, Fourth Edition, 275-290, (1989) McGraw-Hill, N.Y., Publisher.
Yen-Koo, et al., Pharmacol. 25, 111-115 (1982).
Bridges, et al., Ann. Rep. Med. Chem. 23, 39-48 (1988).
Gualtieri, Brain Injury, 2, (2) 101-129, (1988).
van Woerkom, et al., Eur. Neurol. 21, 227-234 (1982).
Haig, et al., Arch. Phys. Med. Rehabil. 71, 1081-1083 (1990).
Williams, J. Med. Chem. 26(5), 619-628 (1983).
Gautier, et al., J. Appl. Physiol. 49(5), 769-777 (1980).
Horn, Arch. Phys. Med. Rehabil. 73, S-317-S-319 (1991).
McLellan, Physical Medicine and Rehabilitation, Sandel et al, Editors, 4(3), 389-407 (Oct. 1990).

*Primary Examiner*—Leonard Schenkman
*Attorney, Agent, or Firm*—Gerald S. Rosen

[57] ABSTRACT

A method of treating comatose patients or near-comatose patients to increase their arousal and alertness as measured by the Glascow Coma Score by administering effective amounts of an adenosine receptor antagonist and a GABA agonist, either concomitantly in any order including simultaneously, or by administering an adenosine receptor antagonist as the sole active agent. The methods of administration are intravenous bolus or drip injection, subcutaneous injection or orally.

10 Claims, No Drawings

METHODS FOR INCREASING AROUSAL AND ALERTNESS AND FOR THE AMELIORATION OF COMATOSE STATES

BACKGROUND

1. Field of Invention

This invention relates to methods and compositions for increasing arousal and alertness of patients in comatose states and for ameliorating such comatose states by the concomitant administration of a compound acting as a gamma-aminobutyric acid (GABA) agonist and a compound acting as an adenosine antagonist, or by the sole administration of a compound acting as an adenosine antagonist.

2. Prior Art

Coma is a state of unconsciousness that is a common and usually immediate sequel of trauma to the head. It is believed to occur because of traumatic damage to axons in the brainstem. These axons are known collectively as the reticular activating system(RAS). The axons project forward to essentially all the major subcortical and cortical brain structures from a diffuse network of cell bodies in the brainstem and thalamus. See Caronna, Rehabilitation of the Head Injured Adult (Eds. Rosenthal, et al.) 59-73, (1983), F. A. Davis, Philadelphia, publisher, and Adams, et al., Principles of Neurology, Fourth Edition, 275-290, (1989), McGraw-Hill, New York.

In mammals, the RAS, when stimulated, appears to produce and maintain a state of heightened arousal and attention to environmental stimuli. See Adams, et al., ibid. It is known that certain adenosine receptor antagonists such as caffeine and theophylline produce marked arousal in cats and rats, and to a lesser extent, in humans. See Yen-Koo, et al., Pharmacol. 25, 111-115, (1982) and Bridges, et al., Ann. Rep. Med. Chem. 23, 39-48, (1988). However, attempts to arouse or improve humans becoming comatose because of head trauma have been limited to administration of agonists or antagonists of the brain neurotransmittersystems for dopamine, acetylcholine, or endorphins, i.e., L-DOPA, levodopa-carbidopa, physostigmine, and naloxone. See Gualtieri, Brain Injury, 2, 101-129, (1988); Van Woerkom, et al., Eur. Neurol. , 21, 227-234, (1982) and Haig, et al. , Arch. Phys. Med. Rehab., 71, 1081-1083, (1990). The aforesaid attempts have generally failed to produce arousal in comatose patients.

There is thus a need for a means to successfully arouse patients who are comatose because of traumatic head injuries.

SUMMARY OF INVENTION

We have discovered that, surprisingly, concomitant administration of effective amounts of an adenosine receptor antagonist and a GABA agonist, or of an adenosine receptor antagonist alone, to persons in a comatose or near comatose state because of traumatic head injuries, results in an increase of alertness and arousal of such persons.

DETAILED DESCRIPTION

The timing of the administration of each compound relative to each other in the case of concomitant administration is not critical, provided all active agents utilized are in the brain at the same time. A preferred concomitant treatment regimen is first to administer a GABA agonist and, before the GABA agonist is out of the brain, to administer the adenosine receptor antagonist. The preferred method of administration of the active agents is by intravenous injection (including intravenous drip); however, other methods of administration are suitable, e.g. oral, intramuscular, subcutaneous, transdermal and the like. The dosage for the adenosine receptor antagonist will vary depending on the clinician's judgment, taking into account the potency of the specific compound or compounds administered, the condition of the patient and the severity of the injury. For example, a suitable dosage for aminophylline when used in combination with a GABA agonist is about 250 mg to about 1750 mg per day, in divided doses of 250 mg given by intravenous injection and 500 mg given by intravenous drip over the subsequent 8-hour period. A suitable dosage for the GABA agonist will vary depending on the clinician's judgment, taking into account the potency of the specific compound or compounds administered, the condition of the patient, the severity of the injury, and the nature and action of the concomitantly administered adenosine receptor antagonist. For example, if ivermectin is the GABA agonist used, a suitable dosage is about 0.8 to about 4 mg/kg of body weight, administered as a single dose and then administered every 3 to 7 days as needed in the judgment of the clinician. If diazepam is used, a suitable dosage is about 40-80 mg per day, administered as a single dose.

The order of administration in the case of concomitant administration is preferably to administer the GABA agonist first and then the adenosine receptor antagonist, in order to lessen the risk of inducing seizures with the adenosine receptor antagonist. However, if the patient is not to be intubated and ventilated artificially, the adenosine receptor antagonist may be administered first in order to lessen the risk of respiratory arrest from the GABA agonist. It is possible to administer simultaneously the active agents, in either two separate dosage forms, e.g. separate injectable solutions, or in a single dosage form, e.g. one injectable solution containing each active ingredient.

The dosage forms used in this invention are those already known to be suitable for use with the active agents of this invention, e.g. sterile injectable solutions, solutions suitable for intravenous drip administration, tablets, capsules and the like. They can be formulated by conventional means using conventional ingredients. The dosage forms of this invention comprise the active agent, i.e. GABA agonist or adenosine receptor antagonist, or a combination thereof, and a compatible pharmaceutically acceptable carrier.

Suitable adenosine receptor antagonists for use in this invention are those compounds that have adenosine receptor antagonist activity due to their ability to block $A_1$ and/or $A_2$ receptors. Examples of typical adenosine receptor antagonist compounds that are suitable for use in this invention are the following xanthines: caffeine, theophylline, 8-phenyltheophylline (8-PT), 8-cyclopentyltheophylline (CPT) and its 1, 3-dipropyl homolog (CPX), the p-PhOCH$_2$CONHCH$_2$NH$_2$ analog of CPX(XAC), the p-PhSO$_2$NMeCH$_2$CH$_2$NMe$_2$ analog of CPX (PD115,199), as well as non-xanthine compounds such as CGS15,943 of the formula

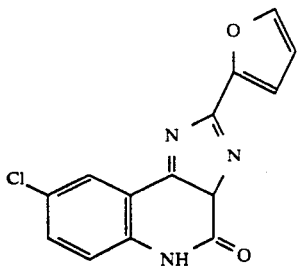

The above adenosine receptor antagonists are discussed in Bridges, et al., Annual Reports in Medicinal Chemistry (Berger, Editor), Chapter 5, pages 39–48 (1988), Academic Press, Inc.

In addition, other adenosine receptor antagonists which are suitable for use in this invention are compounds of the formula
disclosed in U.S. Pat. No. 4,495,187 and 4,547,501, incorporated by reference herein.

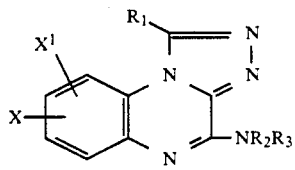

and the pharmaceutically acceptable acid addition salts thereof, wherein

X and $X^1$ are each selected from the group consisting of hydrogen, fluorine, chlorine, bromine and methoxy;

$R_1$ is selected from the group consisting of hydrogen, lower alkyl, lower perfluoroalkyl and phenyl; and $R_2$ and $R_3$ are each selected from the group consisting of hydrogen, lower alkyl, phenylalkyl having up to three carbon atoms in the alkyl moiety and alkanoyl having from two to five carbon atoms, provided that at least one of $R_2$ and $R_3$ is always other than hydrogen when X and $X^1$ are each hydrogen and $R_1$ is hydrogen or methyl; or $R_2$ and $R_3$, when taken together, complete a piperazine ring.

Suitable GABA agonists for use in this invention are compounds which enhance or assist the activity of gamma-aminobutyric acid (GABA). Typical of the GABA agonists that are suitable is the avermectin class of compounds such as ivermectin.

The avermectin family, of which ivermectin, a chemically produced analog, is a member, is a series of compounds isolated from the fermentation broth of a C-076 producing strain of Streptomyces avermitillis, and also chemically produced derivatives thereof. At least eight distinct but closely related compounds are produced by S. avermitillis, $A_{1a}$, $A_{1b}$, $A_{2a}$, $A_{2b}$, $B_{1a}$, $B_{1b}$, $B_{2a}$, and $B_{2b}$. Their production is described in U.S. Pat. No. 4,310,519. The preparation of ivermectin is disclosed in U.S. Pat. No. 4,199,569. The disclosures of each of the foregoing patents are incorporated herein by reference. The avermectin family of compounds is a series of very potent antiparasitic agents known to be useful against a broad spectrum of endoparasites and ectoparasites in mammals and also to have agricultural uses against various nematode and insect parasites found in and on crops and in soil.

Some of the avermectins contain a 22,23-double bond. This may be selectively reduced to prepare the ivermectin compounds. In addition, the avermectins possess a disaccharide moiety at the 13-position consisting of the alpha-L-oleandrosyl-alpha-L-oleandrosyl group. One or both of these saccharide groups may be removed as described in U.S. Pat. No. 4,206,205. The thus produced aglycone derivatives have a hydroxy group at the 13-position. This group may be removed to form the 13-deoxy compound as described in U.S. Pat. No. 4,171,314 and 4,173,571; the latter patent also describes the 13-halo derivatives. The avermectin compounds and derivatives have several hydroxy groups that may be acylated as described in U.S. Pat. No. 4,201,861. Other derivatives of avermectin and ivermectin are disclosed in U.S. Pat. Nos. 4,333,925 and 4,963,667. All the aforementioned patents are incorporated herein by reference.

In addition, the benzodiazepines, a group of synthetic compounds generally used as anticonvulsants, antidepressants, hypnotics and tranquilizers, are suitable GABA agonists for use in this invention. Examples of typical benzodiazepines, which are well documented in the literature, and that are suitable are diazepam, chlordiazepoxide, flurazepam, nitrazepam, oxazepam, medazepam, chlorazepate di-potassium, demoxepam, prazepam, temazepam, quazepam, clonazepam, flunitrazepam, oxazolazepam, ketazolam, tetrazepam, bromazepam, lorprazolam, lorazepam, halazepam, alprazolam, midazolam, lormetazepam, triazolam, trifluadom and Ro 5-4864 of the structural formula

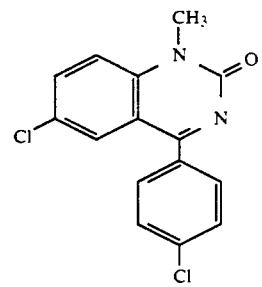

Benzodiazepines are discussed, e.g. in American Society of Hospital Pharmacists, Inc. pages 1333–1356 (1990) and Williams, J. Med. Chem., 26(5), 619–628 (1983). Many of the benzodiazepines listed above are commercially available and are listed in contemporary catalogs, the 1991 Physicians' Desk Reference and The Merck Index, Tenth Edition (1983).

Other GABA agonists that are suitable for use in this invention are baclofen, isoniazid, L-threonine, vigabatrin, gabapentin, valproic acid, zonisamide, muscimol and progabide, In order to determine the ability of the adenosine receptor antagonists, or the combination of one or more adenosine receptor antagonist and one or more GABA agonist, to ameliorate comatose states, standard animal models such as those discussed in Bridges, et al., Ann. Rep. Med. Chem. 23, 39–48 (1988); Gautier, et al., J. Appl. Physiol.: Respirat. Environ. Exercise Physiol., 49(5), 769–777 (1980); Horn Arch. Phys. Med. Rehabil. 72, S-317-S-319(1991) and Adams, et al., Principles of Neurology, Fourth Edition, McGraw-Hill, N.Y., 275-290 (1989) are used.

This invention provides a method not only to cause an increase in alertness and arousal in comatose patients with traumatic head injuries, but in some cases to reverse the coma so that no further treatment is needed.

The following Examples illustrate the invention and are not intended to be limited by the specifics therein.

EXAMPLE 1

Seven patients who were comatose for varying lengths of time following acute head trauma were treated according to the protocols described in the following Table 1. In all cases, assessment of the depth of the coma was made using the Glascow Coma Score as described by Caronna, Ibid. The lowest possible score is 3, completely unresponsive, and the highest possible score is 15, normal alertness. Patients with a score of 8 or less cannot follow verbal commands.

tose. These three patients were treated with a second course of aminophylline, i.e. 500 mg per 8 hours administered by intravenous drip over a 24 hour period. This treatment raised the Glascow Coma Scores in all three cases.

Patient 7, when first seen, had a Glascow Coma Score of 7 and apparently was drunk. The patient was administered 250 mg of aminophylline by intravenous bolus injection and started on an aminophylline drip of 62.5 mg per hour. After three hours, the patient's Glascow Coma Score had risen to 12. The aminophylline was stopped after 8 hours, and by 15 hours after the initial dose of aminophylline, the patient's Glascow Coma Score had risen to 14. In four cases, numbers 2, 3, 4, and 5 as shown in Table 1, the patients continued to be awake and function relatively normally for 24 hours after the last aminophylline infusion was terminated. These patients were terminated from the program and sent home.

TABLE 1

| | Glascow Coma Scores in Patients with Closed Head Injuries | | | | |
|---|---|---|---|---|---|
| Patient No. | Nature of Injury | Time Since Injury | Pre-Drug Glascow Score | Drug Regimen Used* | Post-Drug Glascow Score |
| 1 | L fronto-parietal hemorrhage, diffuse cerebral edema | 11 hrs. | 3 | diazepam (bolus) aminophylline (bolus + drip) | 5 |
| 2 | R basal ganglia hemorrhage, diffuse cerebral edema | 4 hrs. | 6 | diazepam (bolus) aminophylline (bolus + drip) | 8 |
| 2 | | 8 days | 8 | aminophylline (drip) | 14 |
| 3 | L temporoparietal contusion, multiple small hemorrhages | 5 hrs. | 6 | diazepam (bolus) aminophylline (bolus + drip) | 13 |
| 3 | | 4 days | 9 | aminophylline (drip) | 12 |
| 4 | diffuse cerebral edema, multiple small hemorrhages | 4 days | 6 | ivermectin 40 mg (subcutaneous) aminophylline (bolus + drip) | 12 |
| 4 | | 8 days | 10 | aminophylline (drip) | 13 |
| 5 | brainstem contusion | 2 days | 3 | diazepam (bolus) aminophylline (bolus + drip) | 8 |
| 6 | cerebral contusion | 4 hrs. | 8 | diazepam (bolus) aminophylline (bolus + drip) | 13 |
| 7 | R cerebral contusion | 3 hrs. | 7 | aminophylline (bolus + drip) | 12 |

*Diazepam bolus was 50 mg; aminophylline bolus was 250 mg.
Aminophylline drip was 500 mg per 8 hours.

Five patients (Nos. 1, 2, 3, 5 and 6) received a combination of 50 mg diazepam administered by intravenous bolus injection plus 250 mg aminophylline administered by intravenous bolus injection. An aminophylline intravenous drip of 500 mg per 8 hours was then administered for 8 hours to patients 1, 2, 5 and 6, and for 24 hours to patient 3.

Patient 4 was administered 40 mg ivermectin subcutaneously followed by 29,0 mg of aminophylline administered by intravenous bolus injection and administration of 500 mg of aminophylline by intravenous drip over 8 hours. Patient 4 showed an increase of Glascow Coma Score from 6 to 12 by 12 hours after the ivermectin dose.

Patients 2, 3, and 4 showed good initial responses to the GABA agonist plus aminophylline, with increases in Glascow Coma Score from 6 to 8, 6 to 13, and 6 to 12, respectively. However, all three subsequently remained relatively unresponsive and then again became coma-

We claim:

1. A method of increasing the arousal and alertness of comatose patients or near-comatose patients comprising concomitantly administering to the patients effective amounts of an adenosine receptor antagonist and a GABA agonist.

2. The method of claim 1 wherein the adenosine receptor antagonist is administered first.

3. The method of claim 1 wherein the GABA agonist is administered first.

4. The method of claim 1 wherein the adenosine receptor antagonist and the GABA agonist are administered simultaneously.

5. The method of claim 1 wherein the adenosine receptor antagonist is selected from the group consisting of caffeine, theophylline, 8-phenyltheophylline (8-PT), 8-cyclopentyltheophylline (CPT) and its 1, 3-dipropyl homolog (CPX), the p-PhOCH₂CONHCH₂NH₂ analog of CPX(XAC), the p -PhSO₂NMeCH₂CH₂NMe₂ analog of CPX (PD115,199), CGS15,943 represented by the formula

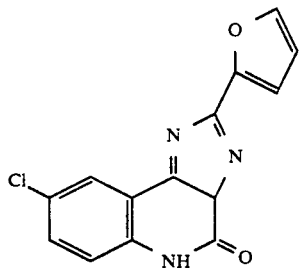

and compounds represented by the formula

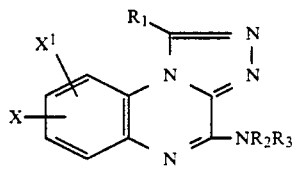

and the pharmaceutically acceptable acid addition salts thereof, wherein

X and X¹ are each selected from the group consisting of hydrogen, fluorine, chlorine, bromine and methoxy;

R₁ is selected from the group consisting of hydrogen, lower alkyl, lower perfluoroalkyl and phenyl; and R₂ and R₃ are each selected from the group consisting of hydrogen, lower alkyl, phenylalkyl having up to three carbon atoms in the alkyl moiety and alkanoyl having from two to five carbon atoms, provided that at least one of R₂ and R₃ is always other than hydrogen when X and X¹ are each hydrogen and R₁ is hydrogen or methyl; or R₂ and R₃, when taken together, complete a piperazine ring.

6. The method of claim 1 wherein the GABA agonist is selected from the group consisting of the avermectins diazepam, chlordiazepoxide, flurazepam, nitrazepam, oxazepam, medazepam, chlorazepate di-potassium, demoxepam, prazepam, temazepam, quazepam, clonazepam, flunitrazepam, oxazolazepam, ketazolapam, tetrazepam, bromazepam, lorprazolam, lorazepam, halazepam, alprazolam, midazolam, triazolam, trifluadom,

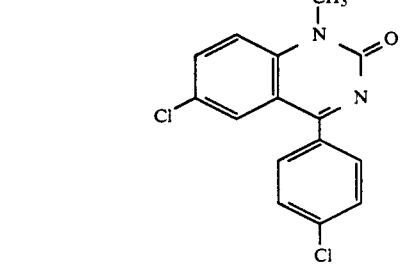

and lormetazepam, and baclofen, isoniazid, L-threonine, vigabatrin, gabapentin, valproic acid, zonisamide, muscimol and progabide.

7. The method of claim 1 wherein the adenosine receptor antagonist is theophylline and the GABA agonist is ivermectin.

8. The method of claim 1 wherein the adenosine receptor antagonist is theophylline and the GABA agonist is diazepam.

9. The method of claim 1 wherein the adenosine receptor antagonist is aminophylline and the GABA agonist is ivermectin.

10. The method of claim 1 wherein the adenosine receptor antagonist is aminophylline and the GABA agonist is diazepam.

* * * * *